US010806839B2

(12) United States Patent
Yomtov et al.

(10) Patent No.: US 10,806,839 B2
(45) Date of Patent: Oct. 20, 2020

(54) PHYSIOLOGICALLY RESPONSIVE VAD FOR CARDIAC EVENTS

(71) Applicant: HeartWare, Inc., Miami Lakes, FL (US)

(72) Inventors: Barry M. Yomtov, Marblehead, MA (US); Fernando Casas, Miami Lakes, FL (US)

(73) Assignee: HeartWare, Inc., Miami Lakes, FL (US)

( * ) Notice: Subject to any disclaimer, the term of this patent is extended or adjusted under 35 U.S.C. 154(b) by 139 days.

(21) Appl. No.: 15/708,998

(22) Filed: Sep. 19, 2017

(65) Prior Publication Data
US 2018/0085506 A1    Mar. 29, 2018

Related U.S. Application Data

(60) Provisional application No. 62/398,647, filed on Sep. 23, 2016.

(51) Int. Cl.
  *A61M 1/10*  (2006.01)
  *A61M 1/12*  (2006.01)

(52) U.S. Cl.
  CPC ........ *A61M 1/1086* (2013.01); *A61M 1/1005* (2014.02); *A61M 1/1029* (2014.02);
  (Continued)

(58) Field of Classification Search
  CPC .............. A61M 1/1005; A61M 1/1029; A61M 1/1086; A61M 1/122; A61M 2205/3303; A61M 2230/04
  See application file for complete search history.

(56) References Cited

U.S. PATENT DOCUMENTS

| 6,234,772 B1 | 5/2001 | Wampler et al. |
| 6,264,635 B1 | 7/2001 | Wampler et al. |

(Continued)

FOREIGN PATENT DOCUMENTS

| EP | 2298375 A1 | 3/2011 |
| WO | 2011090927 A1 | 7/2011 |

(Continued)

OTHER PUBLICATIONS

International Search Report and Written Opinion dated Dec. 12, 2017, for corresponding International Application No. PCT/US2017/052257; International Filing Date: Sep. 19, 2017 consisting of 11-pages.

*Primary Examiner* — Michael W Kahelin
*Assistant Examiner* — Vynn V Huh
(74) *Attorney, Agent, or Firm* — Christopher & Weisberg, P.A.

(57) ABSTRACT

A ventricular assist system including an implantable rotary pump, a pump drive circuit for supplying power to the pump, and a signal processing circuit receiving one or more electrophysiological signals and one or more physiological signals of the subject. The signal processing circuit is operable to receive inputs from the one or more electrophysiological sensors and the physiological sensor, and determine the presence or absence of a non-normal sinus cardiac rhythm condition based on the input from the electrophysiological sensors. In the presence of a non-normal sinus rhythm, the circuit operates the pump in a modified mode of operation. In the absence of a non-normal sinus rhythm, the circuit operates the pump in a normal mode of operation. In either case, the circuit controls the power to the pump and/or speed of the pump based on the input from the physiological sensor and the mode of operation.

9 Claims, 11 Drawing Sheets

(52) U.S. Cl.
CPC ..... *A61M 1/122* (2014.02); *A61M 2205/3303* (2013.01); *A61M 2230/04* (2013.01)

(56) References Cited

U.S. PATENT DOCUMENTS

| | | |
|---|---|---|
| 7,699,586 B2 | 4/2010 | LaRose et al. |
| 2007/0073393 A1* | 3/2007 | Kung ................... A61M 1/101 623/3.13 |
| 2009/0112312 A1 | 4/2009 | LaRose et al. |
| 2012/0245681 A1 | 9/2012 | Casas et al. |
| 2013/0030240 A1* | 1/2013 | Schima ............... A61M 1/1086 600/17 |
| 2013/0338559 A1* | 12/2013 | Franano ............... A61M 1/101 604/4.01 |
| 2014/0100413 A1 | 4/2014 | Casas et al. |
| 2014/0275727 A1* | 9/2014 | Bonde ................. A61M 1/1086 600/17 |
| 2014/0357937 A1 | 12/2014 | Reyes et al. |

FOREIGN PATENT DOCUMENTS

| | | | |
|---|---|---|---|
| WO | WO-2011090927 A1 * | 7/2011 | ............. A61M 1/10 |
| WO | 2016137743 A1 | 9/2016 | |
| WO | 2017053767 A1 | 3/2017 | |

\* cited by examiner

PHYSIOLOGICALLY RESPONSIVE VAD FOR CARDIAC EVENTS

CROSS-REFERENCE TO RELATED APPLICATION

This application is related to and claims priority to U.S. Provisional Patent Application Ser. No. 62/398,647, filed Sep. 23, 2016, entitled PHYSIOLOGICALLY RESPONSIVE VAD FOR CARDIAC EVENTS, the entirety of which is incorporated herein by reference.

STATEMENT REGARDING FEDERALLY SPONSORED RESEARCH OR DEVELOPMENT n/a

TECHNICAL FIELD

The present invention relates to systems and methods for operating ventricular assist devices (VADs).

BACKGROUND

A VAD is a device which is used to assist the heart of a mammalian subject such as a human patient. A typical VAD includes a pump which is implanted in the body of the subject. The pump typically has an inlet connected to a source of blood to be circulated, and an outlet connected to an artery. Typically, the inlet of the pump is connected to the interior of the left ventricle and the outlet of the pump is connected to the aorta, so that the pump operates in parallel with the left ventricle to impel blood into the aorta. The pump may be a miniature rotary impeller pump having an impeller disposed in a pump housing and driven in rotation by a small electric motor which may be closely integrated with the pump. The motor in turn typically is powered by an implantable and/or external power sources such as storage batteries with an arrangement for charging the batteries from an external AC power source. The VAD typically includes a control system which controls operation of the power source so as to drive the impeller at a set rotational speed and thus provide constant pumping action.

VADs can be used to assist the heart of a subject suffering from conditions which impair the pumping ability of the heart. Such assistance can be provided permanently, or while the subject awaits a suitable heart transplant. In other cases, the assistance provided by the VAD allows the heart to heal.

SUMMARY

In one embodiment of the invention, a signal processing circuit for controlling operation of a pump drive operatively coupled to an implantable rotary pump is configured to receive inputs from one or more electrophysiological sensors and a physiological sensor. At least one from the group consisting of the presence and absence of a non-normal sinus cardiac rhythm condition of a patient is determined based on the input from the one or more electrophysiological sensors. When a non-normal sinus rhythm is determined to be present the circuit is configured to instruct the pump drive to operate in a modified mode of operation and control at least one from the group consisting power to the pump drive and speed of the pump based on the input from the physiological sensor and the modified mode of operation. When a non-normal sinus rhythm is determined to be absent the control circuit is configured to instruct the pump drive to operate in a normal mode of operation and control at least one from the group consisting power to the pump drive and speed of the pump based on the input from the physiological sensor.

In another aspect of this embodiment, the signal processing circuit is further configured to control the power supplied to the pump to control the pump speed, and wherein the pump speed has a substantially fixed phase relationship to the electrophysiological signal.

In another aspect of this embodiment, the pump speed has a substantially fixed phase relationship to one from the group consisting of a P-wave, a Q-wave, an R-wave, an S-wave, and a T-wave of a patient's cardiac cycle.

In another aspect of this embodiment, the pump speed has a substantially fixed phase relationship to the R-wave of the patient's cardiac cycle, and the R-wave is determined based on a moving average cycle time averaged over a plurality of cardiac cycles.

In another aspect of this embodiment, the input received from the one or more electrophysiological sensors includes one or more of right atrium, right ventricle, and left ventricle electrograms, and subcutaneous ECG waveforms.

In another aspect of this embodiment, the one or more of right atrium, right ventricle, and left ventricle electrograms, and subcutaneous ECG waveforms, includes at least one waveform derived from a unipolar signal.

In another aspect of this embodiment, the one or more of right atrium, right ventricle, and left ventricle electrograms, and subcutaneous ECG waveforms, includes at least one waveform derived from a bipolar signal.

In another aspect of this embodiment, the input from the physiological sensor is a measurement of left atrial pressure.

In another aspect of this embodiment, the signal processing circuit is further configured to determine whether the measurement of left atrial pressure is one from the group consisting of above, below, and within a predetermined range, and if the measurement of left atrial pressure is above the predetermined range, control an increase of one from the group consisting of the speed and duty cycle of the pump, and if the measurement of left atrial pressure is below the predetermined range, control a decrease of one from the group consisting of the speed and duty cycle of the pump.

In another embodiment, a ventricular assist system includes a rotary pump configured to be implantable with a patient having a heart, the rotary pump is in fluid communication with the heart and the systemic circulation of the patient to assist blood flow from the heart to the systemic circulation. A pump drive circuit for supplying power to the pump and controlling the speed of the pump is included. A signal processing circuit for controlling operation of a pump drive operatively coupled to an implantable rotary pump is included and configured to receive inputs from one or more electrophysiological sensors and a physiological sensor. At least one from the group consisting of the presence and absence of a non-normal sinus cardiac rhythm condition of a patient is determined based on the input from the one or more electrophysiological sensors. When a non-normal sinus rhythm is determined to be present the circuit is configured to instruct the pump drive to operate in a modified mode of operation and control at least one from the group consisting power to the pump drive and speed of the pump based on the input from the physiological sensor and the modified mode of operation. When a non-normal sinus rhythm is determined to be absent the control circuit is configured to instruct the pump drive to operate in a normal mode of operation and control at least one from the group consisting power to the pump drive and speed of the pump based on the input from the physiological sensor.

In another aspect of this embodiment, the system further includes one or more electrophysiological sensors for sensing one or more electrophysiological signals of the patient; and a physiological sensor for sensing a physiological property of the heart.

In another aspect of this embodiment, the one or more electrophysiological sensors includes at least one from the group consisting one or more electrogram and subcutaneous electrocardiogram sensors.

In another aspect of this embodiment, the physiological sensor includes one or more pressure transducers.

In yet another embodiment, a signal processing circuit for controlling operation of an implantable rotary pump includes an input module for receiving one or more electrophysiological signals of a patient from one or more electrophysiological sensors and a processor for processing the received electrophysiological signals. The processor is configured to determine one from the group consisting of the presence and absence of a tachy-arrhythmia condition based on the one or more electrophysiological signals, and in the presence of a tachy-arrhythmia condition, control operation of the pump in a tachy-arrhythmia mode. The processor is further configured to determine one from the group consisting of the presence and absence of a bradycardia condition based on the one or more electrophysiological signals, and in the presence of the bradycardia condition, control operation of the pump in a bradycardia mode. The processor is further configured to determine one from the group consisting of the presence and absence of a reduction in cardiac blood flow condition based on the one or more electrophysiological signals, and in the presence of the reduction in cardiac blood flow condition, control operation of the pump in a reduced cardiac blood flow mode.

In another aspect of this embodiment, the tachy-arrhythmia condition is one from the group consisting of a ventricular tachy-arrhythmia and an atrial tachy-arrhythmia.

In another aspect of this embodiment, the reduced cardiac blood flow condition is one from the group consisting of an ischemia condition and a myocardial infarction condition.

In another aspect of this embodiment, the processor is configured to determine whether to operate in one from the group consisting of a non-pulsatile mode and a pulsatile mode based on the one or more electrophysiological signals, wherein the non-pulsatile and pulsatile modes control the pump to run in one from the group consisting of a non-pulsatile or pulsatile manner, respectively.

In another aspect of this embodiment, in the non-pulsatile mode, the signal processing circuit controls power supplied to the pump and varies pump speed based the non-normal sinus cardiac rhythm condition of the patient.

In another aspect of this embodiment, in the pulsatile mode, the signal processing circuit controls an increase in pump speed for increased cardiac output, and determines whether to operate one from the group consisting of synchronously and asynchronously with the cardiac cycle of the patient based on the one or more electrophysiological signals.

In another aspect of this embodiment, in the pulsatile mode, the signal processing circuit determines whether to operate in one from the group consisting of a co-pulsation mode and a counter-pulsation mode based on the one or more electrophysiological signals.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
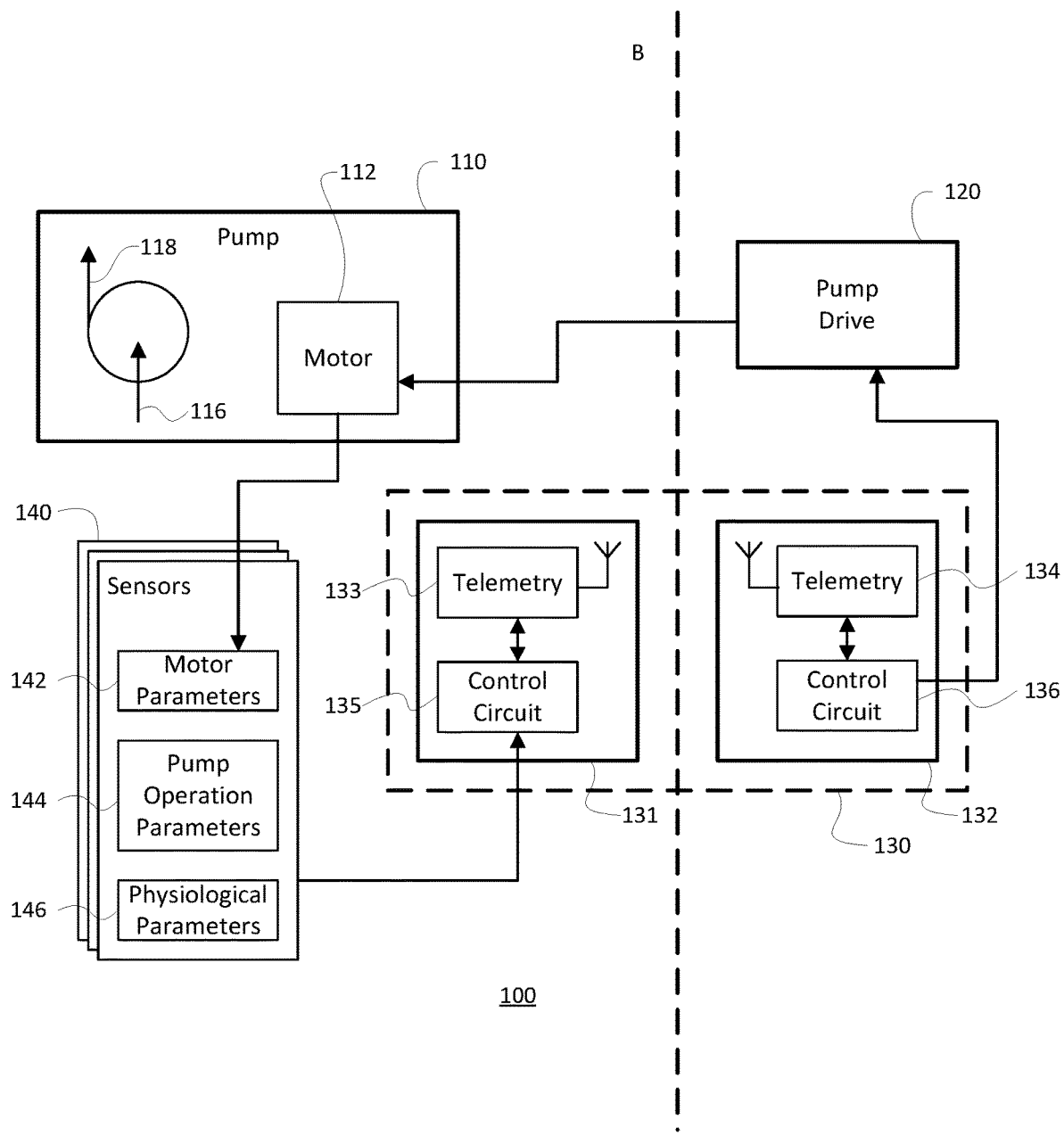
FIG. 1 is a functional block diagram of a ventricular assist system having a VAD in accordance with an aspect of the present disclosure.

Referring now to the drawings in which like reference designators refer to like elements, there is shown in FIG. 1 an implantable blood pump system 100 constructed in accordance with the principles of the present invention and designated generally "100." The blood pump system 100 may include a VAD, such as a rotary pump 110, incorporating a motor 112, that is implantable within the body B of a patient. The term "rotary pump" refers herein to a pump which incorporates a pumping element mounted for rotation in a housing.

The pump 110 may be a rotary impeller pump having an impeller mounted within a housing, so that the spinning motion of the impeller transfers momentum to the fluid to be pumped. Although the pump 110 and motor 112 are depicted as separate components for clarity of illustration in FIG. 1, in practice these components can be closely integrated with one another. For example, the impeller of the pump 110 may serve as the rotor of the motor 112.

The motor 112 may be a multi-phase brushless direct current, permanent magnet motor arranged to drive the impeller of the pump 110 at a rotational speed prescribed by the motor driver by means of a motor commutation technique such as trapezoidal commutation. These components are arranged so that the pump 110 can be implanted within the body of a mammalian subject such as a human patient, with the inlet 116 in fluid communication with a ventricle of the heart, such as the left ventricle, and with the outlet 118 in fluid communication with an artery, such as the aorta. For example, the pump 110 may be arranged for implantation outside of the heart, and the inlet and outlet may include conduits that can be surgically connected to the ventricle and the aorta. In other arrangements, the pump 110 is arranged so that it may be implanted within the aorta and ventricle. Exemplary implantable pumps are described in detail in U.S. Pat. Nos. 6,264,635, 6,234,772 and 7,699,586; and US Patent Publication No. 20090112312. These patents and published patent applications, which are commonly assigned, are hereby incorporated by reference.

The system 100 may also include a pump drive circuit 120. The pump drive circuit 120 may include ports for one or more output connections and one or more input connections, an electrical storage battery and a motor driver to control the motor. The motor driver may include semiconductor switching elements which are responsive to control signals applied at a control input, so that the current supplied to motor 112 can be controlled. An output connection, such as a cable, may connect the pump drive circuit 120 to the motor 112 of pump 110, so that the motor driver can drive the motor 112 and thus operate the pump 110. In the example of FIG. 1, the pump drive circuit 120 is mounted outside of the patient's body B and is operatively connected to the motor 112 by one or more conductors that penetrate the skin of the patient. In other arrangements, the pump drive circuit may be implanted within the patient's body and may be connected to an external power source using inductive coupling or skin-penetrating conductors, such that the connection between the pump drive circuit and motor does not need to penetrate the patient's skin.

The system 100 may also include a signal processing circuit 130. In the example of FIG. 1, the signal processing circuit 130 is connected to the pump drive circuit 120 to control operation of the pump drive circuit 120, and thereby control operation of the pump 110. The signal processing circuit 130 is also connected to one or more sensors 140 to receive inputs from the sensors, such that operation of the pump may in turn be based on sensor data.

In the example of FIG. 1, the signal processing circuit 130 includes both an internal module 131 implanted inside of the patient's body B, and an external module 132 mounted outside of the patient's body B. The modules 131 and 132 may be connected to one another by a suitable signal transmitting arrangement, such as the radio frequency telemetry transmitting/receiving units 133 and 134 shown in FIG. 1, so that signals and data may be interchanged between the modules. Modules 131 and 132 may include conventional data processing elements such as one or more control circuits 135 and 136. The distribution of hardware elements and software functions between these control circuits 135 and 136 can vary. At one extreme, all of the data processing necessary to perform the monitoring and control methods described herein may be performed by the control circuit 136 of the external module 132, with the internal module 131 acting essentially as a conduit for relaying data and signals from the motor 110 to the external module 132 or vice versa. At the other extreme, all of the data processing may be performed by the control circuit 135 of the internal module 131, with the external module acting essentially as a conduit for relaying data and signals from the internal module 131 to the pump drive circuit 120. In such an example, if the pump drive circuit is implanted within the patient's body, the external module 132 may be omitted entirely. Aside from the above extreme examples, given the internal and external modules 131 and 132 capability to relay data and signals between one another, it is well within the ability of those skilled in the art to provide for some data processing to be performed by the control circuitry of one module, while the remaining data processing is performed by the control circuitry of the other module.

The internal module 131 may be connected to receive power from the alternating current supplied by the pump drive circuit 120 to motor 112. The power required to operate the circuitry of the internal module 131 is typically about 3 orders of magnitude less than the power required to drive motor 112. This arrangement is particularly useful where the internal module 131 is physically located in the vicinity of the pump 110, such as being physically coupled to and/or housed in a housing of the pump. In such cases where the internal module 131 of the signal processing circuit 130 is physically located in the vicinity of the pump 110, it may be desirable to provide magnetic shielding between the coils of the pump motor 112 and the circuitry of the internal (implanted) module 131. In other arrangements, the internal module 131 may be positioned apart from the pump 110. In such arrangements, the signal processing circuitry 130 may receive power from an internal battery (not shown), such as a primary battery or rechargeable battery.

The sensors 140 of the system 100 may include one or more sensors for monitoring operating conditions of the pump 110 and/or physiological conditions of the patient. With regard to the pump 110, one or more sensors may indicate motor parameters 142, such as motor speed or angular position (phase). For instance, a back electromotive force ("back EMF" or "BEMF") detector operable to detect voltage or current in the stator coils of motor 112 may provide a measurement of motor speed or load. In some instances, other sensors may be included to indicate pump operation parameters 144 such as flow rate of blood exiting the pump, and/or pressure differential across the pump. In other instances, a control circuit 135 and/or 136 may be programmed to determine these features based on other parameters of the pump, such as motor current and/or BEMF. Examples of flow rate and pressure determinations based on BEMF are described in detail in US Patent Publication Nos. 2012/0245681, 20140100413, 20140357937. These patents and published patent applications, which are commonly assigned, are hereby incorporated by reference.

The one or more sensors may also indicate physiological parameters 146, including but not limited to oxygen concentration, pressure within a vessel or chamber, temperature, and parameters related to cardiac demand (e.g., heart rate, stroke volume). The sensors may include, for instance, pressure transducers arranged to provide signals indicative of left atrial pressure (LAP). LAP is an input parameter for basis of the Starling control of the heart. As LAP rises, so does cardiac output. Therefore, monitoring LAP could be used to determine whether cardiac output (and thereby pump flow) should be increased or decreased. This information can be used in the determination of the optimal therapeutic response of changing the pump speed and/or the duty cycle.

Figure 2:
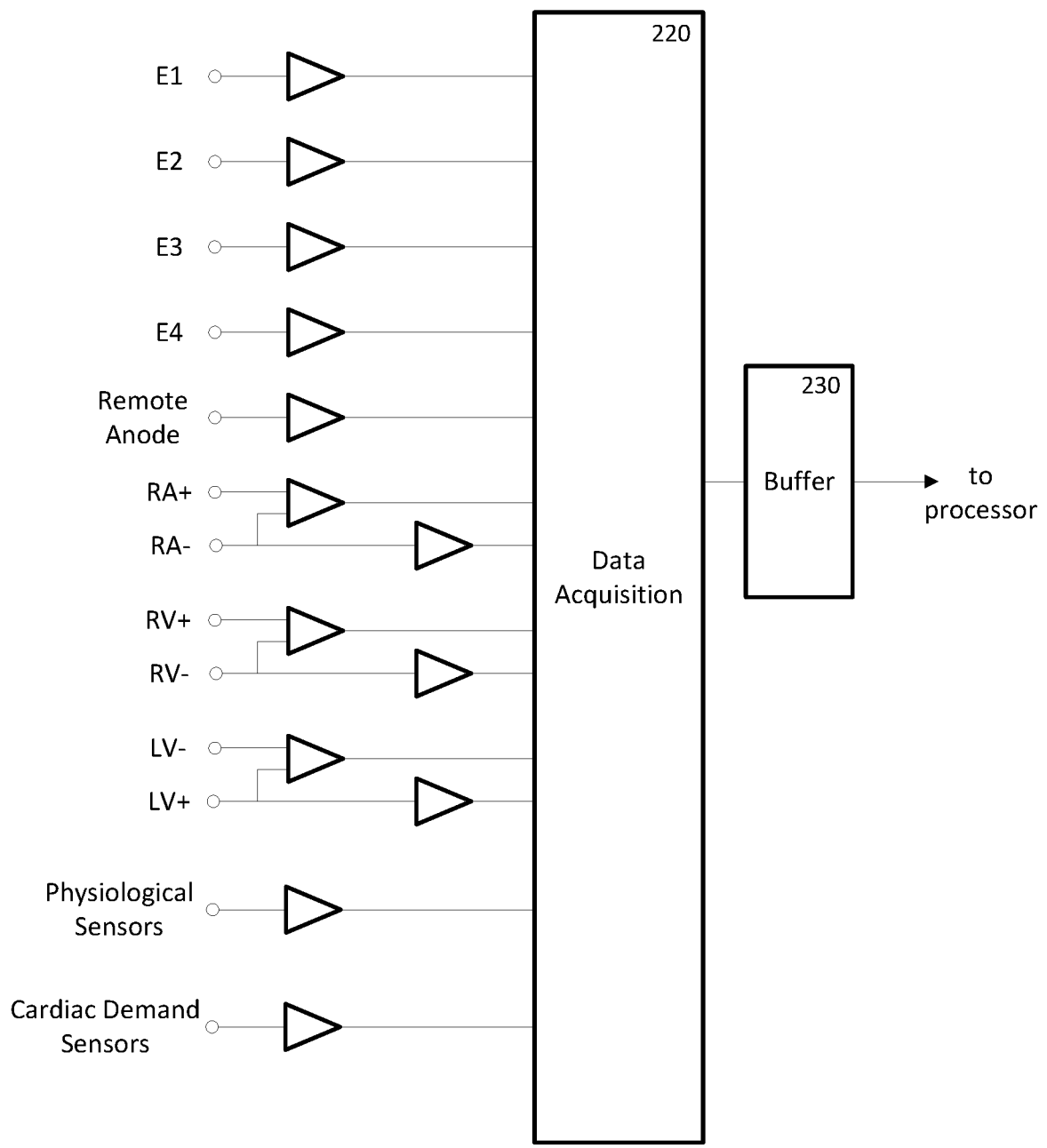
FIG. 2 is a schematic diagram depicting a portion of the system of FIG. 1.

FIG. 2 illustrates an example input 200 of various sensor data to the internal module 131 of the signal processing circuit 130. The sensor data may be fed into the internal module 131 of the signal processing circuit 130 through appropriate signal conditioning elements such as an analog to digital converter 220 and buffer memory 230.

Figure 3:
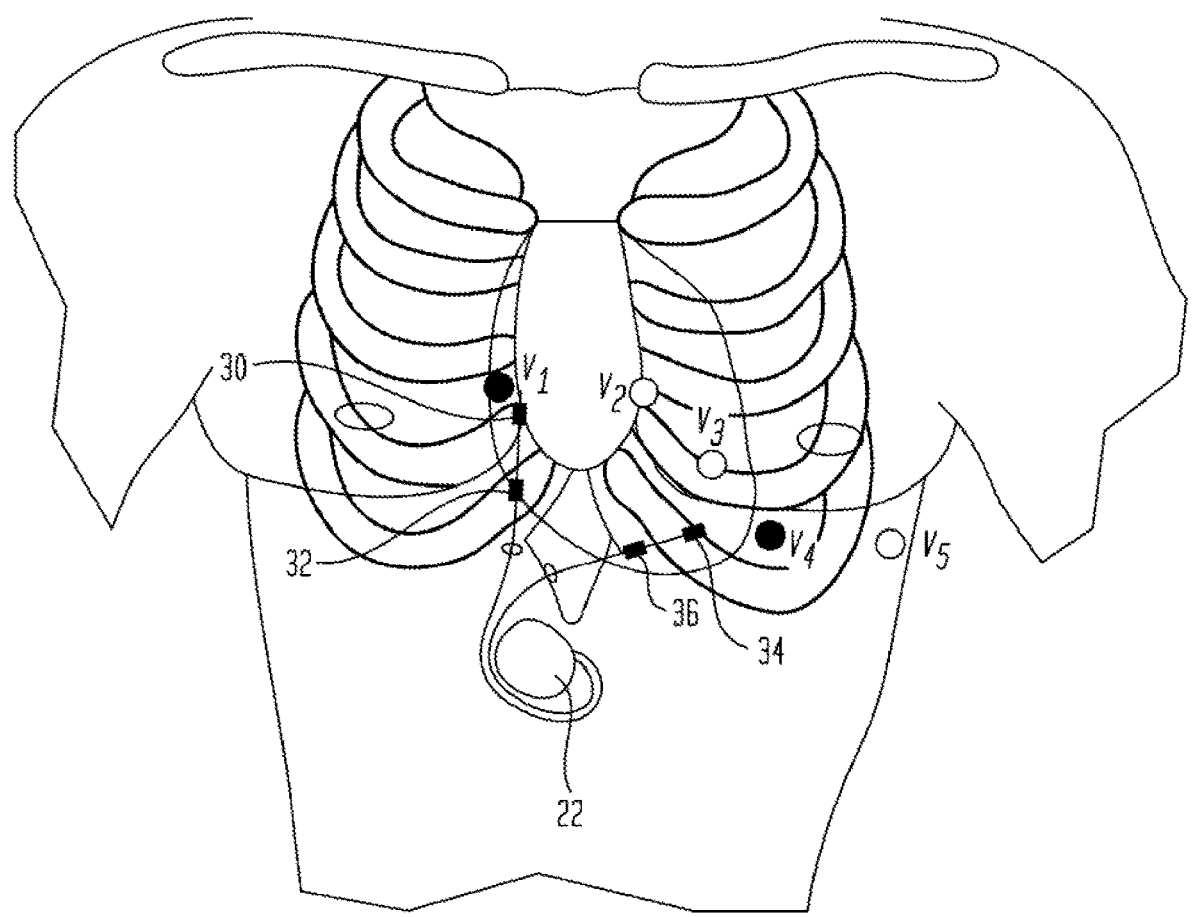
FIG. 3 is a diagram depicting lead and subcutaneous electrode implantations in accordance with an aspect of the present disclosure.

As shown in FIG. 2, the sensor data may include data sensed by transvenously implanted electrodes which may provide electrogram data. Some electrogram data may include data provided from bipolar electrode pairs, such as electrode pairs RA+/RA−, RV+/RV−, and LV−/LV+, which are connected to the right atrium (RA), right ventricle (RV) and left ventricle (LV) of the patient, respectively. Other data may be received from ECG signals. The term ECG refers to electrophysiological signals sensed from the heart which may be received from implanted electrodes or electrodes on the outer skin surface of a patient. The ECG signals may be subcutaneous ECG (sECG) signals E1, E2, E3 and E4 sensed by pre-cordial electrodes connected to various pre-cordial (or chest) locations in the patient's body. An example of the respective locations that the pre-cordial electrodes E1, E2, E3 and E4 (labeled 30, 32, 34 and 36, respectively) may be connected to within the patient's body is shown in FIG. 3 similar to a 12-lead surface ECG designations V1, V2, V3, V4 and V5. ECG surface electrodes may also be used to provide the electrophysiological data to the control system, as in a 12-lead ECG electrode configuration.

The sensor data may be further supplemented by a ground electrode or remote anode connectable to a location remote from the heart. This electrode could provide a ground reference for use with those signals derived from unipolar electrodes (e.g., the pre-cordial electrodes shown in FIG. 2). For instance, the anode may be a far field remote anode, such as the conductive titanium case of the implanted electronics 22 when implanted remotely from the pump 110 as shown in FIG. 3.

The sensor data may further include data received from physiological sensors and cardiac demand sensors (used for gathering the physiological parameters 146 described in connection with FIG. 1).

It is not essential to provide all of the cardiac electrodes shown in FIG. 2. For example, where the bipolar signals are used for control of the system, the unipolar electrodes may optionally be omitted.

The control circuit(s) 135 and/or 136 (or, more generally, the signal processing circuit 130) may be configured to receive, analyze and process sensor data, and determine a physiological condition of the patient based on this analysis. Signal processing may involve: determining the phase of the patient's cardiac cycle; sensing the patient's intrinsic heart rate; determining the patient's metabolic demand; detecting the presence of a cardiac arrhythmia; and detecting a reduction of blood flow to the heart during conditions of ischemia or (during a more significant reduction) myocardial infarction. The signal processing circuit 130 may further respond to the processed signal data by controlling the pump 110, such as by setting an appropriate mode of operation and/or speed of the pump 110. The signal processing circuit 130 may also control the frequency of the motor drive signal to the pump 110.

Figure 4:
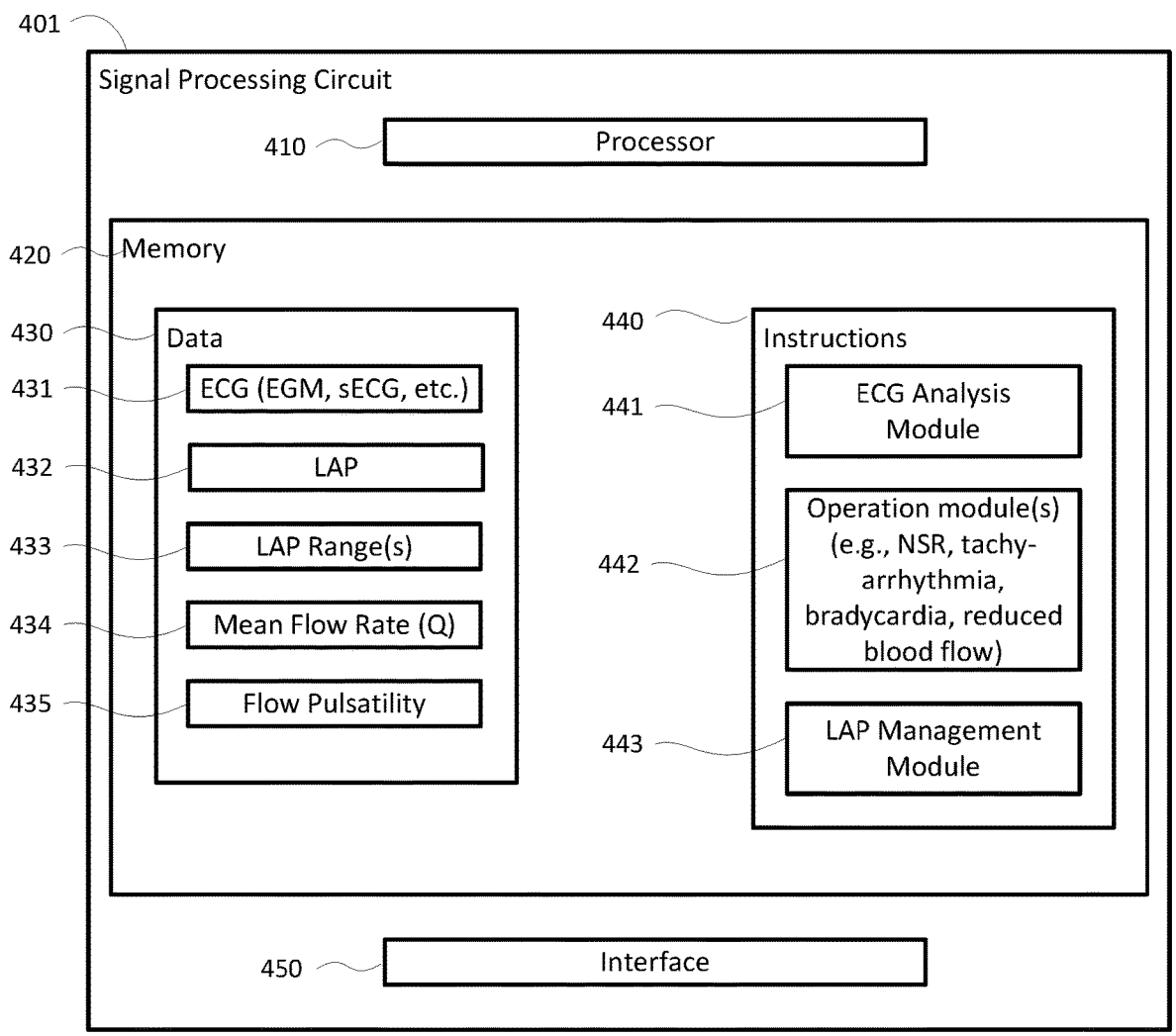
FIG. 4 is a block diagram of a control circuit in accordance with an aspect of the present disclosure.

FIG. 4 is a functional block diagram 400 of an example signal processing circuit 401 in accordance with one aspect of the disclosure. As explained above, the functions described in connection with FIG. 4 may be included in the internal control circuit 135, the external control circuit 136, or distributed therebetween. Additionally, certain functions may be included in both control circuits.

The signal processing circuit 401 may include a processor 410. The processor 410 may be hardware that performs one or more operations. By way of example only, one or more control units (not shown) coupled to an arithmetic logic unit (ALU) (not shown) and memory 420 may direct the signal processing circuit 401 to carry out program instructions 440 stored in memory 420 at a particular clock rate. The processor 410 may be any standard processor, such as a central processing unit (CPU), a dedicated processor, such as an application-specific integrated circuit (ASIC), a microcontroller, custom integrated circuit (IC), or field programmable gate array (FPGA). While one processor block is shown, the signal processing circuit 401 may also include multiple processors which may or may not operate in parallel.

Memory 420 stores information accessible by processor 410 including instructions 440 for execution by the processor 410 and data 430 which is retrieved, manipulated or stored by the processor 410. The memory 420 may be of any type capable of storing information accessible by the processor, such as a hard-drive, ROM, RAM, flash memory (EEPROM), CD-ROM, write-capable, read-only, or the like.

Data 430 may be retrieved, stored or modified by processor 410. Although the data of the present disclosure is not limited by any particular data structure, the data 430 may be stored in computer registers, in a relational database as a table having a plurality of different fields and records such as chronological events and/or data loops, or the like. The data 430 may also be formatted in any computer readable format such as, but not limited to, binary values, ASCII or EBCDIC (Extended Binary-Coded Decimal Interchange Code). Moreover, any information sufficient to identify the relevant data may be stored, such as descriptive text, proprietary codes, pointers, or information which is used by a function to calculate the relevant data.

The data 430 may include data received from one or a combination of the sensors described herein. By way of example, such data may include electrocardiogram (ECG) signals 431 such as electrogram (EGM) and/or subcutaneous electrocardiogram (sECG), and LAP measurements 432. The data 430 may also include pre-stored ranges, thresholds and other values used for analyzing and otherwise processing the received data signals. For instance, the data may include LAP range information 433 indicating desirable ranges of LAP under various conditions. The LAP range information may be stored in a table or other data structure by which various physiological or pump conditions may be associated with acceptable ranges of LAP.

The data 430 may further include values derived based on an analysis of the received signals. For instance, flow rate information, such as a plurality of instantaneous flow rate values over a span of time, may be received by the signal processing circuit and analyzed to determine a mean flow value 434 over a given span of time. The mean flow value 434 may then be stored in the data 430. For further instance, the flow rate information may be used to determine flow pulsatility 435. In some examples, the flow rate information may itself be determined (e.g., based on BEMF) and/or stored.

The instructions 440 may include any set of instructions to be executed directly (such as machine code) or indirectly (such as scripts) by the processor 410. In that regard, the terms, "algorithms", "instructions," "steps" and "programs" may be used interchangeably herein.

The instructions 440 may include one or more modules for analyzing or processing the received data. For example, an ECG analysis module 441 may perform various analyses of a received sECG waveform, e.g., P-wave, R-wave, QRS complex, ST segment, etc. As explained in greater detail below, analysis of the sECG waveform may be utilized to determine a particular physiological condition of the patient's heart, which in turn may be utilized to determine an appropriate mode of operation for the pump (or more generally, for the system). The instructions 440 may also include one or more operation modules 442, each operation module containing a set of instructions for operating the pump (or system) according to a respective mode of operation.

For further example, an LAP management module 443 may analyze information relating to LAP of the patient. As discussed in greater detail below, such an analysis may determine whether the patient's LAP is within an appropriate range (e.g., based on LAP range information 433 stored in the data 430), and if necessary, may in some cases even control the pump (or system) to help bring the patient's LAP back into an appropriate range.

The signal processing circuit 401 includes one or more interfaces 450 for connecting to inputs (e.g., sensors 140) and outputs (e.g., pump drive circuit 120). The interfaces 450 may include wired and/or wireless connections (e.g., near field electromagnetic coupling or far field RF such as MICS). For components of the signal processing circuit 401 that are adapted to be disposed within the body of the patient, the interface 450 may include known elements for communicating signals through the skin of the patient.

Under normal circumstances, the patient's heart functions with normal sinus rhythm (NSR). Under such circumstances, the signal processing circuit may receive ECG signals such as sECG and/or EGM indicating NSR of the heart, and in turn may operate in an NSR mode. In the NSR mode, the signal processing circuit actuates the pump drive circuit to vary the speed of the pump in synchrony with the detected cardiac activity.

Figure 5A:
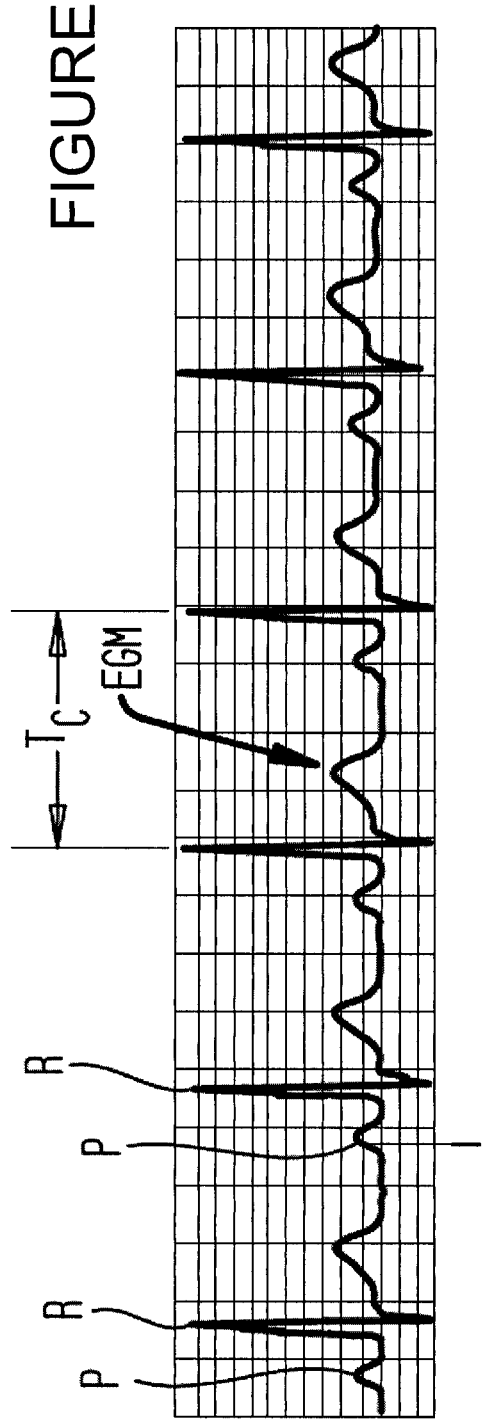
FIGS. 5A and 5B are graphs of certain signals and variables occurring in operation of a VAD in accordance with an aspect of the present disclosure.
Figure 5B:
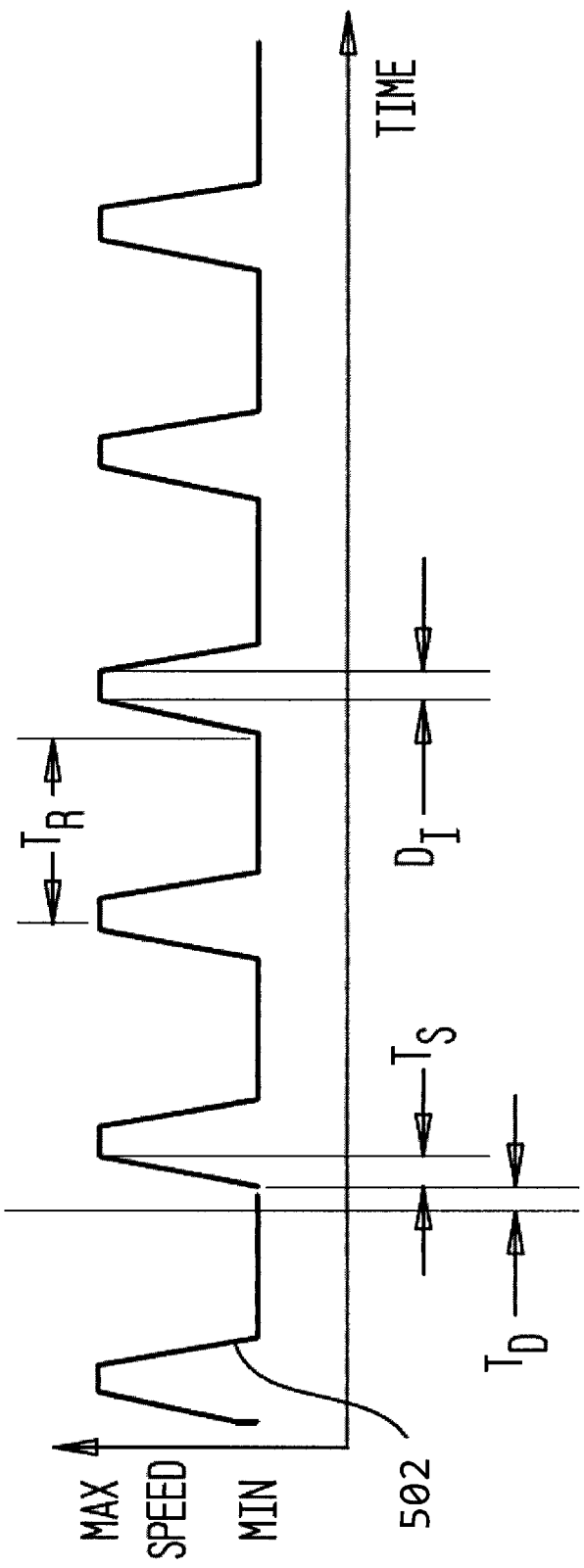

FIGS. 5A and 5B depict an ECG signal having a normal sinus cardiac rhythm and a plot of motor speed, respectively. The ECG curve shown in FIG. 5A is a schematic depiction showing a conventional external electrocardiogram waveform, representing a composite of electrical signals in the heart. In practice, the actual received sECG signals are separate signals, with each implanted electrode (e.g., electrodes 30, 32, 34 and 36 of FIG. 3) providing additional electrical vectors of the cardiac contraction as indicated during the QRS complex of the heart beat. Additionally, while FIG. 5A shows ECG signals, those skilled in the art should appreciate that sECG and/or EGM electrophysiological signals may be utilized to control operation of the pump. The sECG and/or EGM signals may further be recorded and stored in memory for future analysis and review by a physician.

In FIG. 5B, the signal processing circuit actuates the pump drive circuit to vary the speed of the pump between a minimum speed and a maximum speed, as depicted by the curve in FIG. 5B. Curve 502 depicts the speed variation as a progressive ramp-up from minimum to maximum, followed by operation at maximum, followed by ramp-down to minimum and operation at minimum. However, the pattern of speed variation can be more complex, with the speed continuously varying during the entire cycle. For example a co-pulsation or counter-pulsation method can be used to synchronize the pump speed to the cardiac cycle. The pattern of variation in the speed of the pump is synchronized with the intrinsic rhythm of the patient's heart so that the variation in speed of the pump has a substantially fixed phase relationship to the intrinsic rhythm of the heart.

In the co-pulsation method, the pump operates at the maximum speed during ventricular systole, when the ventricles contract to expel blood and at the minimum speed during ventricular diastole, when the ventricles relax to fill with blood. As ventricular systole occurs during the R-wave of the ECG signal (representing ventricular depolarization), the pump reaches maximum speed at a time close to the timing of the R-wave. Thus, the pump generally operates at maximum speed during ventricular systole, when the ventricles contract to expel blood.

In the counter-pulsation method, the pump speed increases during the ventricular filling (diastole) and is at minimum speed during ventricular systole.

Synchronization (e.g., synchronizing the pump speed to the cardiac cycle in the co-pulsation method) may be achieved using one or more of the following techniques.

The signal processing circuit may store a slew time $T_S$ (shown in FIG. 5B). The mechanical components of the pump have inertia and require a finite time equal to $T_S$ in order to accelerate from minimum speed to maximum speed. To compensate for this delay, the signal processing circuit may actuate the pump drive circuit to progressively increase speed of the pump over a period of time equal to $T_S$.

The signal processing circuit can also determine the cycle time $T_C$ of the cardiac cycle, which is simply the inverse of the heart rate. Based on $T_C$, the signal processing circuit can further determine a time $T_R$, where $T_R = T_C - T_S$, corresponding to the beginning of the R-wave of the preceding cardiac cycle. The signal processing circuit can then initiate the increase in the pump speed at the time $T_R$. Provided that the heart rate is constant or varying slowly, and that the signal processing circuit updates the heart rate and recalculates $T_C$ frequently, this simple arrangement can yield reasonable synchronization of the pump speed increase with the onset of ventricular systole. The cycle time $T_C$ used in the calculation can, for example, be based on a moving average of the cycle time over a few previous cycles.

Alternatively or additionally, the signal processing circuit can measure the synchronization achieved during each cardiac cycle and advance or retard the initiation of pump acceleration accordingly. For example, if $T_R$ is determined to be short in the preceding cycle (such that the pump reaches full speed before the R-wave), the signal processing circuit can increase $T_R$ for the next cycle. In this regard, the signal processing circuit can act as a phase-locked loop holding the pump speed waveform in synchronization with the intrinsic cardiac cycle of the patient. In one arrangement, the cyclic variation of pump speed has a fixed phase relationship to the R-wave. In a variant arrangement, the measurement of synchronization can be a moving average representing the last few cardiac cycles.

In normal sinus rhythm, there is a substantially constant interval from the P-wave to the R-wave in each cardiac cycle. This interval can be estimated from the heart rate or can be determined directly from measurement of the ECG signals (e.g., EGM signals, sECG signals). Thus, the signal processing circuit can determine a period of time $T_D$ (show in FIG. 5B) after each P-wave and initiate pump acceleration at the end of $T_D$. $T_D$ may be selected to equal the P-wave to R-wave interval minus $T_S$. In some instances, $T_S$ may be equal to the P-wave to R-wave interval, in which case $T_D$ may be zero. In this arrangement, the cyclic variation of pump speed has a fixed phase relationship to the P-wave.

Other features of the ECG signals can be used as the basis for synchronization. Software routines for recognizing individual features of the waveforms such as the P-wave, and QRS complex of ECG signals are well known, and any of such routines can be used in a synchronization scheme such as those schemes described above.

The signal processing circuit can also utilize other electrophysiological signals as the basis for synchronization. An ECG signal of the left ventricle using subcutaneous electrodes (such as sECG electrodes 34 and/or 36) may also provide timing information regarding the ventricular depolarization. The signal processing circuit can then actuate the pump drive circuit to increase the speed of pump, each time the left ventricle signal indicates beginning of ventricular depolarization.

Synchronizing operation of the VAD with the patient's intrinsic depolarization allows the pump to operate when it is most advantageous to do so. Cardiac output is greatest during contraction of the atria and ventricles. In a weak or diseased heart, contraction of the chambers, and particularly the left ventricle is when assistance from a VAD is most critical. Therefore controlling the timing of the pump to be in synchrony with ventricular contraction provides an optimal assistance to the patient and maximizes the therapeutic effect of the VAD. Moreover, operation in a pulsatile mode synchronized to the subject's cardiac cycle can improve efficiency and thus conserve power.

While the synchronization of the pump can be triggered by the actual occurrence of a signal, it is also possible to program the signal processing circuit to anticipate the impending occurrence of such a signal. For example, it is well known that each phase of the cardiac cycle should last for approximately the same duration of time in healthy patients. The signal processing circuit could be programmed to measure historical patient data and store the measured data in a memory. For instance, the measured and stored data may comprise an indication of $T_C$ (cardiac cycle length). Measurements taken and stored over time can then be used to determine through any mathematic or statistical means known, when the next phase of the cardiac cycle should begin in a given patient. This would allow the signal processing circuit to instruct the pump drive circuit when to accelerate the pump, based on an anticipation of an upcoming cardiac cycle. Furthermore, because atrial and ventricular systole is signaled by the beginning of the P-wave and R-wave respectively, the historical analysis of these phases of the cardiac cycle could be used to predict the onset of systole.

This predictive method of synchronizing the pump with an actual or anticipated signal is of particular use in patients suffering from left side heart failure. Left side heart failure is a challenging pathology predominantly affecting the left ventricle. Patients with left side heart failure require assistance in order to maximize the efficiency of the left ventricular contraction. In one embodiment, the signal processing circuit may receive ECG signal information (e.g., EGM signals, sECG signals) from a patient with left sided heart failure. The signal processing circuit then analyzes the ECG signal information and determines when an R-wave is occurring or is about to occur. Upon detecting the occurrence or impending occurrence of the R-wave, the signal processing circuit instructs the pump drive circuit to operate the motor in order to drive the pump in synchrony with the patient's own ventricular systole.

For each cardiac cycle, the signal processing circuit may also specify a desired duration of time $D_1$ (shown in FIG. 5B) for which the pump operates at maximum speed. $D_1$ may be defined based on the previous measurements of the patient's R-waves. Alternatively, $D_1$ can be defined based on a fixed proportion of the cardiac cycle time $T_C$. In yet another variant, $D_1$, or the routine used to set $D_1$, can be programmed into the signal processing circuit by a physician. Typically, $D_1$ is selected such that the pump operates at maximum speed during most or all of ventricular systole.

Either or both of the maximum speed of the pump and the $D_1$ may be set as fixed values, or can be varied by the signal processing circuit based on sensed data (e.g., ECG or other electrophysiological signals, LAP or other physiological condition sensors, cardiac demand sensor, or combinations thereof, etc.) indicating the current status of the patient. The fixed speed may vary from patient to patient, and may be predetermined by a clinician. The varied speed may involve varying a maximum and/or minimum speed. For example, the maximum speed may increase with the heart rate as determined by the sensed data. Thus, the maximum speed may vary depending on whether the patient is sleeping, awake, and/or exercising. The minimum speed typically is a non-zero speed, such that the pump runs continually but speeds up and slows down during each cycle. For example, some rotary impeller pumps utilize hydrodynamic bearings to maintain a pump rotor out of contact with a surrounding pump housing, so that the pump operates with zero wear on the rotor and housing. These hydrodynamic bearings become ineffective when the rotor speed falls below a threshold low pump operating speed. When the pump incorporates such bearings, the minimum speed set by the signal processing circuit is desirably set at or above the threshold low pump operating speed. The minimum speed can also vary depending on sensed data.

Figure 6:
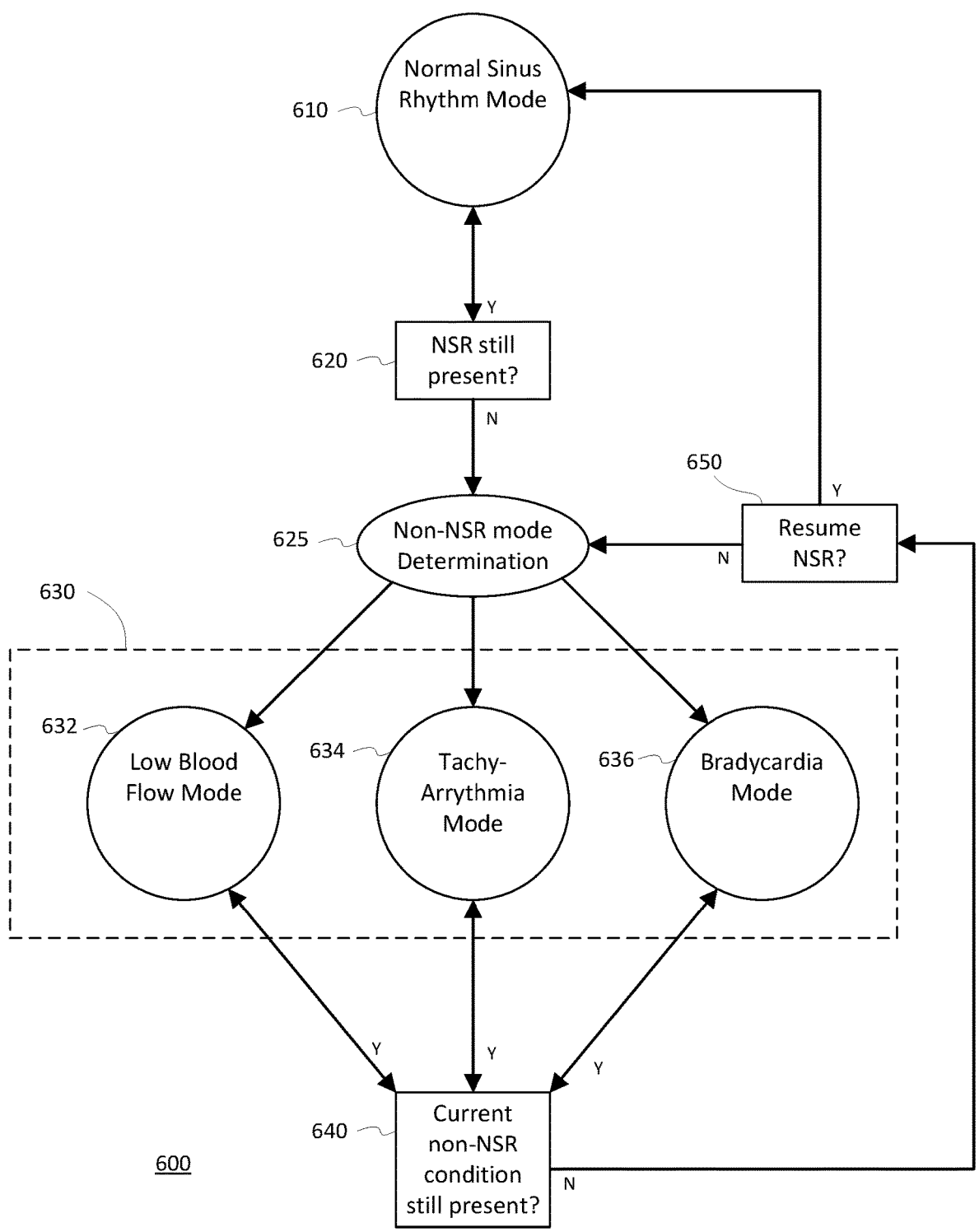
FIG. 6 is a flowchart depicting operating mode determinations for a VAD in accordance with an aspect of the present disclosure.

FIG. 6 is a flow diagram 600 depicting an example operation for a signal processing circuit to determine an appropriate mode of operation of the system. In the example of FIG. 6, operation of the pump begins in the Normal Sinus Rhythm Mode 610. At 620, the signal processing circuit determines whether to remain in Normal Sinus Rhythm Mode 610 based on received physiological and/or pump data, pre-stored data, or a combination thereof. If the signal processing circuit determines to remain in Normal Sinus Rhythm Mode 610, operations in Normal Sinus Rhythm Mode 610 may continue. If the signal processing circuit determines at 620 not to remain in Normal Sinus Rhythm Mode 610, operations may continue at 625, in which the signal processing circuit determines which non-NSR mode 630 to enter Like the detection of (or in this case, absence of) Normal Sinus Rhythm Mode 610, the non-NSR mode 630 determination may be based on received data, prestored data, or a combination thereof.

Depending on the determination at 625, the signal processing circuit may enter any one of a low blood flow mode 632, a tachy-arrhythmia mode 634 or a bradycardia mode 636. From the non-NSR mode 630, the signal processing circuit may continue to receive physiological data and at 640 determine whether operation should remain in the current non-NSR mode 630. If it is determined that operation should remain in the current non-NSR mode 630, then operation may continue with the currently active non-NSR mode 630 (e.g., low cardiac blood flow mode 632, a tachy-arrhythmia mode 634 or a bradycardia mode 636). If it is determined that the current non-NSR mode condition has cleared, then at 650 it is determined whether the Normal Sinus Rhythm Mode 610 should be resumed. If so, then operation may revert to 610 with resumption of the Normal Sinus Rhythm Mode. Otherwise, a different non-NSR mode 630 (e.g., low cardiac blood flow mode 632, a tachy-arrhythmia mode 634 or a bradycardia mode 636) is selected at 625.

Figure 7:
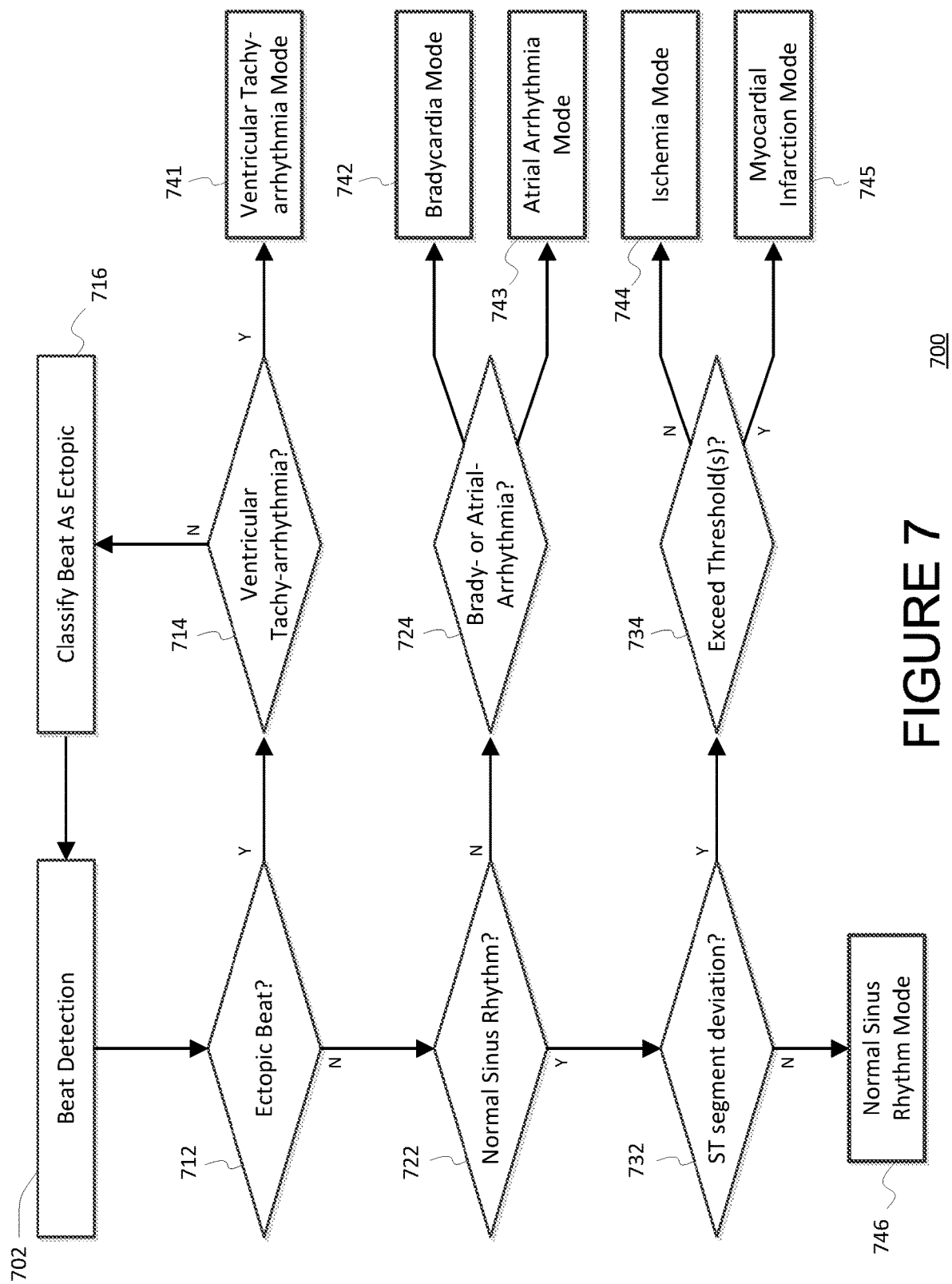
FIG. 7 is a flow chart depicting control of a VAD based on cardiac rhythm determinations in accordance with an aspect of the present disclosure.

FIG. 7 is a flow diagram 700 providing a detailed example of how the operations shown in FIG. 6 may be executed on a beat-by-beat basis. At 702, the signal processing circuit performs a beat detection of the patient's heart. Beat detection may be based on pre-cordial subcutaneous electrode signals, similar to 12 lead ECG cardiac monitors. Any detection circuit or algorithm routine which is effective to detect a normal sinus beat versus an ectopic (non-sinus) beat can be programmed into the signal processing circuit. For example, the signal processing circuit may receive an ECG (e.g., sECG) signal and detect the patient's cardiac rhythm based on the ECG signal. The signal processing circuit may further use the beat detection signal (e.g., sECG signal) to identify irregularities in the patient's cardiac rhythm.

At 712, the beat detection is used to determine whether the patient has a disturbance in the cardiac rhythm, such as an ectopic beat. If an ectopic beat is detected, then at 714, a determination is made whether the patient has a ventricular tachy-arrhythmia based on the previously recorded and classified beats (e.g., a sequence of ventricular ectopic beats may be indicative of ventricular tachy-arrhythmia). If the patient has a detected ventricular tachy-arrhythmia, then the signal processing circuit may instruct the pump drive to operate in a ventricular tachy-arrhythmia mode 741. In the ventricular tachy-arrhythmia mode 741, the pump may be controlled in a pulsatile asynchronous mode, and may increase pump speed or duty cycle. If the rhythm is not determined to be a ventricular tachy-arrhythmia, then at 716 the previously detected beat is recorded as ectopic of origin, and the signal processing circuit continues with detecting the next beat at 702.

If an ectopic beat is not detected, then at 722, the signal processing circuit determines whether or not the detected beats indicate a normal sinus rhythm. If a normal sinus rhythm is not detected, then at 724, the signal processing circuit continues with determining whether the detected beat is indicative of bradycardia arrhythmia or an atrial-arrhythmia such as atrial tachycardia or atrial fibrillation. Depending on the determination at 724, the signal processing circuit may instruct the pump drive to operate in either one of a bradycardia mode 742 or an atrial-arrhythmia mode 743.

If a normal sinus rhythm is detected at 722, the signal processing circuit may further analyze further aspects of the detected beat to determine whether the pump drive should operate in the normal sinus rhythm mode or in a different mode for addressing other non-rhythm-related cardiac issues. At 732, signal processing circuit analyzes whether the ST segment of the ECG signal has a deviation in amplitude (e.g., elevation or depression). The deviation may be measured by comparing the ST segment to a predetermined amplitude. This predetermined amplitude may be pre-stored in the memory, or may be derived, at least in part, by calculating a moving average of multiple detected normal sinus beats. If there is a deviation in the ST segment by greater than a predetermined amount, then at 734, the signal processing circuit may determine to operate the pump drive in a mode associated with reduced cardiac blood flow condition (e.g., ischemia).

The signal processing circuit may be capable of determining the degree of deviation in the ST segment by comparing the ST segment deviation to multiple threshold values. For instance, a first threshold value may indicate that an ischemic reduction of blood flow to the cardiac muscle has occurred, while a second threshold value greater than the first or an alternative waveform deviation may indicate a myocardial infarction. The deviation not exceeding the second threshold value would be indicative of ischemia, and the signal processing circuit may instruct the pump drive to operate in an ischemia mode 744.

In one example, the ischemia mode may be a constant-speed mode in which the pump runs at a constant speed such that the pump speed does not vary during the cardiac cycle. The signal processing circuit actuates the pump drive circuit to supply power at a constant frequency to the motor, so that the pump operates at a constant speed. The constant speed may be less than the maximum speed used during pulsatile operation. Additionally, while the pump speed is generally substantially constant over the course of a given cardiac cycle, the signal processing circuit is capable of altering the constant speed over a longer scale of time (e.g., from one cardiac cycle to the next) depending on a patient condition sensed by the physiologic sensor.

If the ST segment deviation exceeds the second threshold value, such deviation could be indicative of myocardial infarction, and the signal processing circuit may instruct the pump drive to operate in a myocardial infarction mode 745. In one example of a myocardial infarction mode, the signal processing circuit may switch the pump drive to a constant speed in order to increase the cardiac output for increased blood flow to the cardiac muscle.

Alternatively, either or both of the ischemia and myocardial infarction modes may be a pulsatile mode in which variation of the pump speed is synchronized to the sinus beats. The signal processing circuit may include an algorithm for selecting between the pulsed mode (synchronous or asynchronous) or constant speed mode in response to detection of an ischemia condition or myocardial infarction condition, and further depending on conditions such as metabolic demand or left atrial pressure. For instance, the signal processing circuit may determine to begin the ischemia mode with asynchronous pulsed operation of the pump drive (and optionally transition to synchronous operation), whereas for the myocardial infarction mode, the signal processing circuit may begin with pulsed synchronous operation of the pump drive.

Lastly, if the patient's heart is determined at 732 to have a normal sinus rhythm, and it is further determined that there is no significant deviation in the ST segment, then the processing circuit may instruct the pump drive to operate in a normal sinus rhythm mode 746. The normal sinus mode 746 may involve operation of the pump in either one of a continuous flow mode or a pulsatile mode (synchronous or asynchronous (e.g., qPulse, Lavare)).

Operation in the any of the above-described modes 741-746 may continue until the signal processing circuit determines a change in the cardiac rhythm, or reduced cardiac blood flow of the patient. In some cases, additional factors may be considered in determining whether to switch from one mode of operation to another (e.g., additional physiological parameters, an amount of time spent in a given mode, etc.).

The signal processing circuit may be configured to identify additional conditions, and consequently operate in additional modes. For instance, if a tachycardia arrhythmia is detected, the signal processing circuit may be further configured to differentiate between any of a ventricular tachycardia ("VT") (mode 741, discussed above), ventricular fibrillation ("VF"), atrial fibrillation ("AF"), and supraventricular tachycardia ("SVT"). In a VF mode, the signal processing circuit may operate the pump in either a continuous or pulsatile asynchronous mode, whereas in either an AF or SVT mode, the signal processing circuit may instruct the pump drive to operate in a pulsatile asynchronous mode. For further instance, if a bradycardia arrhythmia is detected, the signal processing circuit may be configured to differentiate between any of a sinus bradycardia, bradycardia heart block, total third degree heart block, or asystole. In yet a further instance, if an atrial arrhythmia is detected, the signal processing circuit may be configured to differentiate between an atrial tachycardia and atrial fibrillation. In any of these events, the signal processing circuit may instruct the pump drive to operate in a pulsatile asynchronous mode, but in the event of a bradycardia heart block, the pump drive may further be controlled to increase its speed, whereas in the event of an asystole, the pump drive may further be controlled to increase its duty cycle.

The routine of FIG. 7 may be conducted repeatedly, regardless of the mode in which the signal processing circuit has instructed the pump drive to operate. For instance, if the signal processing circuit switches the pump drive to operate in an ischemia mode, it may still continue to execute beat detection 702 and the ST segment measurements 732 to determine whether the ischemia condition has ended.

With a long term implant like a VAD, the ECG, sECG, EGM or other electrophysiological data gathered under condition of a normal sinus rhythm may be collected and stored in memory. The stored data may then be used to give an indication of what qualifies as a normal sinus rhythm for a given patient. The stored data may further be updated by the signal processing circuit on a continuous basis to reflect changes to the baseline waveform and rhythm (indicative of physiological changes to the patient). Similar data may be collected and utilized for other patient conditions aside from NSR.

In addition to the signal processing circuit's capability of determining various pump operation modes based on cardiac activity of the patient, the signal processing is also capable of independently monitoring and controlling pump operation based on left atrial pressure of the patient. As discussed above, the signal processing circuit may store or otherwise access a range of acceptable left atrial pressure values, and may speed up or slow down the pump in order to keep the patient's left atrial pressure within this range.

Figure 8:
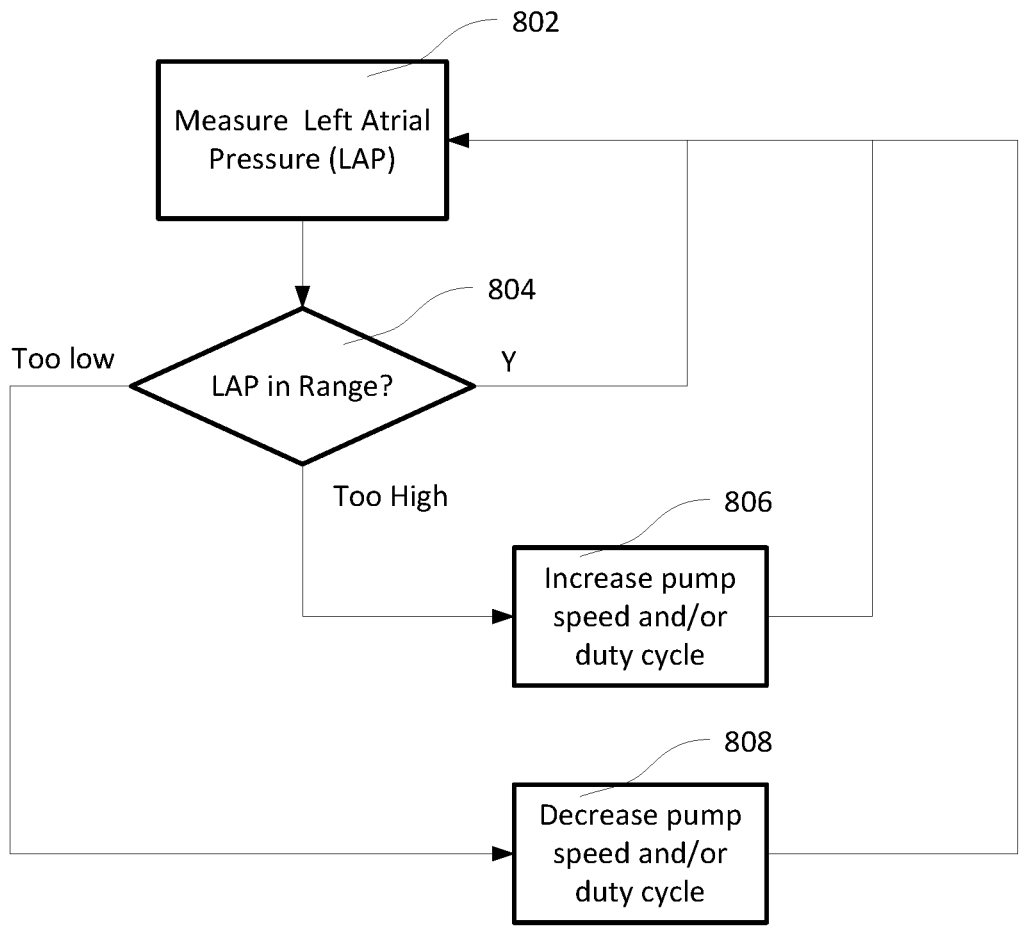
FIG. 8 is a flow chart depicting control of a VAD based on left atrial pressure (LAP) determinations in accordance with another aspect of the present disclosure.

FIG. 8 is a flow diagram 800 providing an example of how the signal processing circuit may control pump operation to keep a patient's left atrial pressure (LAP) within range. At 802, the signal processing circuit receives an LAP measurement. The LAP measurement may be received from a physiological sensor, such as one or more pressure transducers. At 804, the signal processing circuit compares the LAP measurement to a prestored range and determines whether the measurement is within range. If the LAP measurement is within range, no adjustments to the pump are made.

If the LAP measurement is determined to exceed the acceptable range, then at 806, the signal processing circuit adjusts pump operation to increase the output of the pump. For instance, pump speed may be increased. Additionally, or alternatively, an amount of power provided to the pump (e.g., a duty cycle of a pulse width modulated power source) may be increased.

If the LAP measurement is determined to be below the acceptable range, then at 808, the signal processing circuit adjusts pump operation to decrease the output of the pump. For instance, pump speed may be decreased. Additionally, or alternatively, an amount of power provided to the pump (e.g., a duty cycle of a pulse width modulated power source) may be decreased.

In any of the above cases, this process may be repeated with subsequent measurements of LAP at 802.

In some situations, what may be an acceptable LAP range for a patient having type of cardiac function (e.g., normal sinus rhythm) may not be an acceptable range for another type of cardiac function (e.g., ischemia). Therefore, the signal processing circuit may be configured to store or access multiple LAP ranges, each range being suitable for a different cardiac condition. For instance, measured LAP may be compared to a different LAP range depending on the mode of operation as determined by the signal processing circuit.

Figure 9:
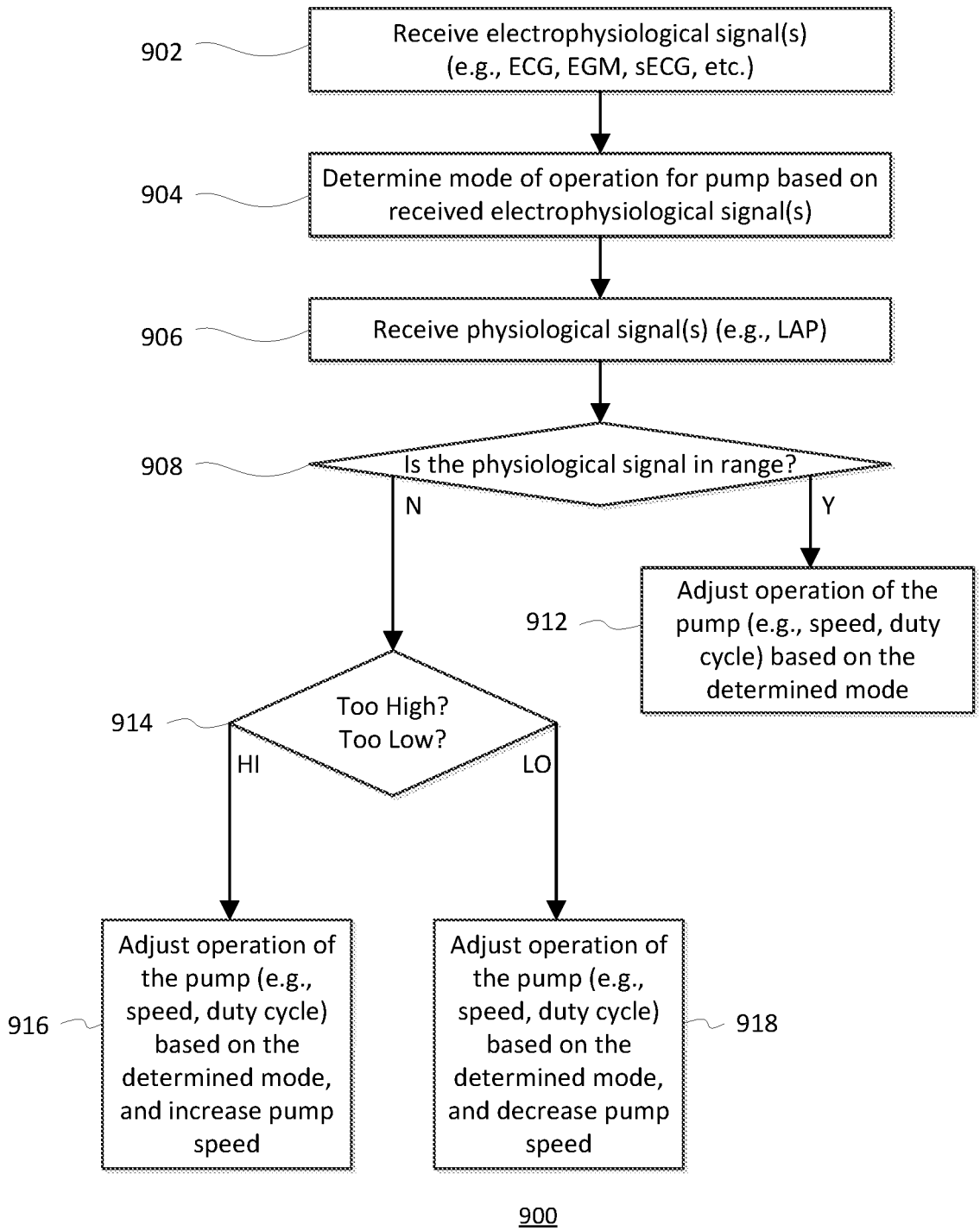
FIG. 9 is a flow chart depicting control of a VAD based on LAP and cardiac rhythm determinations in accordance with another aspect of the present disclosure.

FIG. 9 provides a flow diagram 900 providing an example of how the signal processing circuit may control both mode of operation of the pump and manage LAP (or another physiological parameter having an acceptable range) using the same routine. At 902, the signal processing circuit receives one or more electrophysiological signals, such as ECG (e.g., sECG and/or EGM) signals. Based on the received electrophysiological signals, at 904, the signal processing circuit determines a desired mode of operation for the pump drive. This determination may be performed using the routine shown in the flow diagram 700 of FIG. 7. At 906, the signal processing circuit receives one or more physiological signals, such as LAP. At 908, the physiological signal is compared to a predetermined range, and the signal processing circuit determines whether the physiological signal is in range. As mentioned above, the specific range for comparison to the physiological signal may be selected based on the mode of operation determined at 904. If it is determined that the physiological signal is in range, then at 912, operation of the pump drive is adjusted (if necessary) based solely on the determined mode of operation.

If, however, it is determined that the physiological signal is not within range, then at 914, the signal processing circuit further determines whether the physiological signal is greater than or less than the range. If the physiological signal is greater than the range, then at 916, operation of the pump drive is adjusted based on the determined mode of operation as well as pump speed or duty cycle being increased (for LAP and possible alternative physiological signals) or decreased (for other physiological signals) in order to compensate for the too-high physiological signal. If the physiological signal is less than the range, then at 918, operation of the pump drive is adjusted based on the determined mode of operation as well as pump speed or duty cycle being decreased (for LAP and possible alternative physiological signals) or increased (for other physiological signals) in order to compensate for the too-low physiological signal.

Figure 10:
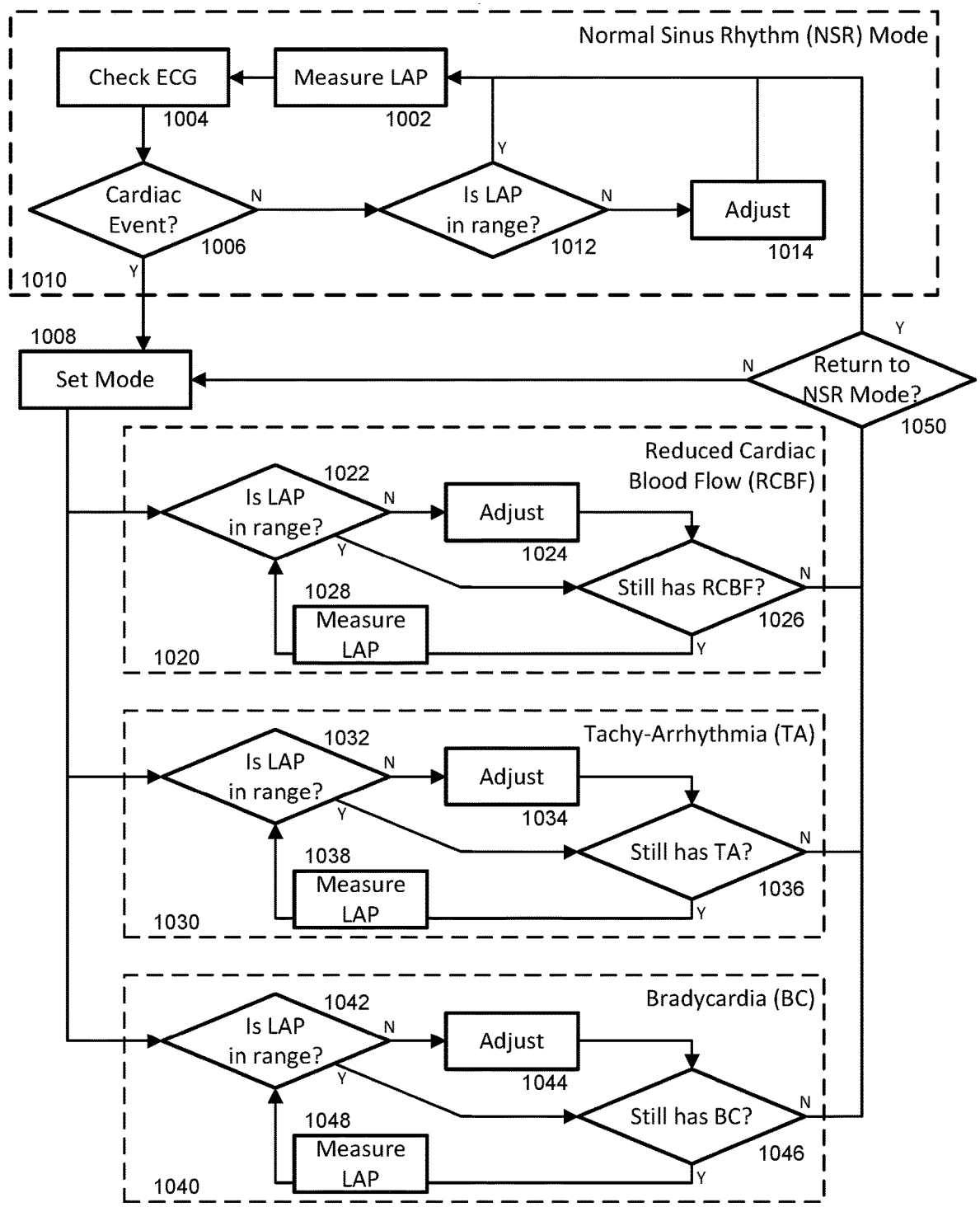
FIG. 10 is another flow chart depicting control of a VAD based on LAP and cardiac rhythm determinations in accordance with another aspect of the present disclosure.

FIG. 10 is a flow diagram 1000 providing an example of how the signal processing circuit may continuously control both mode of operation and manage LAP in the same routine. For sake of clarity, description of the example of FIG. 10 begins with the signal processing circuit operating in a normal sinus rhythm mode. However, because the operations of FIG. 10 are repeatedly performed (e.g., in a continuous loop) while the pump is in operation, there is no specific beginning or ending point to the flow diagram.

At 1002, the signal processing circuit receives a measurement of LAP. At 1004, the signal processing circuit receives an ECG signal, such as EGM or sECG. At 1006, the signal processing circuit detects the presence of a cardiac event. In one example, detection of a cardiac event may be based on an analysis of the ECG signal, as shown in the flow diagram 700 of FIG. 7. If no cardiac event is detected, the signal processing circuit continues to instruct the pump drive to operate in the normal sinus rhythm mode 1010, and at 1012, determines whether the measured LAP is within an acceptable range. If LAP is not in an acceptable range, then operations continue at 1014 and operation of the pump drive (e.g., pump speed, duty cycle) is adjusted to bring LAP within range. The adjustment may be controlled in the manner described in connection with FIG. 8. If LAP is already within range, then operations may subsequently continue at 1002 and 1004 with further LAP and ECG measurements.

If a cardiac event is detected at 1006, then at 1008, the signal processing circuit selects which mode (e.g., a reduced cardiac blood flow mode 1020, a tachy-arrhythmia mode 1030, a bradycardia mode 1040) to operate in. Operations then continue in the selected mode. In each mode, at one of 1022, 1032 or 1042, the measured LAP (from 1002) is compared with a predetermined LAP range for the selected mode. If the measured LAP is determined to be outside of the LAP range, then at 1024, 1034 or 1044, operation of the pump is adjusted (as in 1014), and operations then continue at 1026, 1036 or 1046. If at 1022, 1032 or 1042, the measured LAP is determined to be within the LAP range, then the signal processing circuit may skip 1024, 1034 or 1044, and continue directly with 1026, 1036 or 1046.

The signal processing circuit then continues operations at 1026, 1036 or 1046 and determines whether the previously detected condition has persisted. In some examples, determining persistence of a condition may involve receiving and analyzing an updated electrophysiological signal. The analysis may be comparable to the analysis performed at 1006 and 1008. If it is determined that the condition has persisted, then operations may continue at 1028, 1038 and 1048, with no change of the pump drive's mode of operation and with subsequent measurement of LAP, and then at 1022, 1032 or 1042, with a further determination of whether the newly measured LAP is or is not in range. Otherwise, if the previously detected condition is determine to no longer exist, then operations may continue at 1050, with a determination of whether the NSR mode may resume. If the NSR mode can be resumed, operations may continue at 1002. Otherwise, a non-NSR mode (different from the previously selected mode) is determined and the signal processing circuit instructs the pump drive to operate in the determined non-NSR mode 1008.

Figure 11:
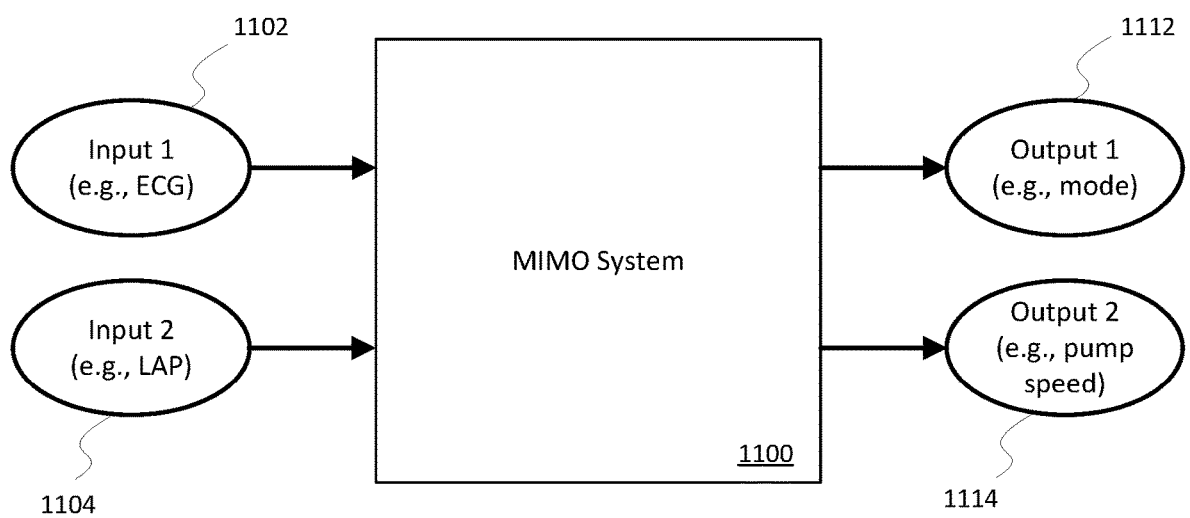
FIG. 11 is a multiple-input multiple-output system for controlling operation of a VAD in accordance with an aspect of the present disclosure.

The example system 1100 of FIG. 11 is arranged to be capable of executing the routine of FIG. 10. The system 1100 may be thought of as a multiple-input multiple-output (MIMO) system, including at least a first input 1102 indicative of a cardiac rhythm or cardiac blood flow condition (based on the analysis of an electrophysiological signal), a second input 1104 indicative of cardiac output (based on flow measurement, LAP measurement, etc.), a first output 1112 indicative of a determination of a desired mode of pump flow (e.g., continuous flow, synchronous pulsatility, co-pulsation, counter-pulsation, asynchronous pulsatility, etc.), and a second output 1114 indicative of a desired average flow (e.g., increase/decrease motor speed, increase/decrease duty cycle, etc.). Based on the first and second outputs 1112/1114, the system 1100 may further select a mode of operation and operational parameters (and/or an acceptable range thereof) for the pump. The outputs may be updated up to as frequently as the inputs are received in order to provide continuous control of the VAD. In this manner, not only electrophysiological (e.g. ECG) signals but even LAP measurements may be used to manage various patient conditions, such as non-sinus rhythms, heart blockages, and reduced cardiac blood flow.

While various elements have been described above as individual components depicted in functional block diagrams, these elements can be combined with one another. Conversely, elements shown as unitary elements in the functional block diagrams discussed above can be separated into separate elements. Also, the features described above with reference to different embodiments of the invention can be combined with one another.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A signal processing circuit for controlling operation of a pump drive operatively coupled to an implantable rotary pump, the signal processing circuit configured to:
   receive inputs from one or more electrophysiological sensors and a physiological sensor configured to measure left atrial pressure;
   determine at least one from the group consisting of the presence and absence of a non-normal sinus cardiac rhythm condition of a patient based on an electrogram measurement from the one or more electrophysiological sensors; and
   when a non-normal sinus rhythm is determined to be present:
      instruct the pump drive to operate in a modified mode of operation; and
      control at least one from the group consisting of power to the pump drive and speed of the pump based on a left atrial pressure measurement from the physiological sensor and the modified mode of operation; and
   when a non-normal sinus rhythm is determined to be absent:
      instruct the pump drive to operate in a normal mode of operation; and
      control at least one from the group consisting of power to the pump drive and speed of the pump based on the left atrial pressure measurement from the physiological sensor;
   operate in a co-pulsation mode, the co-pulsation mode configured to operate the pump at maximum speed during ventricular systole and at minimum speed during ventricular diastole; and
   operate in a counter-pulsation mode, the counter-pulsation mode configured to operate the pump at maximum speed during ventricular diastole and at minimum speed during ventricular systole.

2. The circuit of claim 1, wherein the signal processing circuit is further configured to control the power supplied to the pump to control the pump speed, and wherein the pump speed has a fixed phase relationship to the electrophysiological signal.

3. The circuit of claim 2, wherein the pump speed has a fixed phase relationship to one from the group consisting of a P-wave, a Q-wave, an R-wave, an S-wave, and a T-wave of a patient's cardiac cycle.

4. The circuit of claim 3, wherein the pump speed has a fixed phase relationship to the R-wave of the patient's cardiac cycle, and the R-wave is determined based on a moving average cycle time averaged over a plurality of cardiac cycles.

5. The circuit of claim 1, wherein the electrogram received from the one or more electrophysiological sensors includes one or more of right atrium, right ventricle, and left ventricle electrograms, and subcutaneous ECG waveforms.

6. The circuit of claim 5, wherein the one or more of right atrium, right ventricle, and left ventricle electrograms, and subcutaneous ECG waveforms, includes at least one waveform derived from a unipolar signal.

7. The circuit of claim 5, wherein the one or more of right atrium, right ventricle, and left ventricle electrograms, and subcutaneous ECG waveforms, includes at least one waveform derived from a bipolar signal.

8. A ventricular assist system, comprising:
   a rotary pump configured to be implantable with a patient having a heart, the rotary pump being configured to be in fluid communication with the heart and a systemic circulation of the patient to assist blood flow from the heart to the systemic circulation;

a pump drive circuit for supplying power to the pump and controlling a speed of the pump; and a signal processing circuit for controlling operation of the pump drive circuit operatively coupled to the rotary pump, the signal processing circuit configured to:
receive inputs from one or more electrophysiological sensors and a physiological sensor configured to measure left atriai pressure;
determine at least one from the group consisting of the presence and absence of a non-normal sinus cardiac rhythm condition of the patient based on an electrogram from the one or more electrophysiological sensors; and
when a non-normal sinus rhythm is determined to be present:
 instruct the pump drive circuit to operate in a modified mode of operation; and
 control at least one from the group consisting of power to the pump drive circuit and the speed of the pump based on a left atrial pressure measurement from the physiological sensor and the modified mode of operation; and
when a non-normal sinus rhythm is determined to be absent:
 instruct the pump drive circuit to operate in a normal mode of operation; and
 control at least one from the group consisting of power to the pump drive circuit and the speed of the pump based on the left atrial pressure measurement from the physiological sensor;
 operate in a co-pulsation mode, the co-pulsation mode configured to operate the pump at maximum speed during ventricular systole and at minimum speed during ventricular diastole; and
 operate in a counter-pulsation mode, the counter-pulsation mode configured to operate the pump at maximum speed during ventricular diastole and at minimum speed during ventricular systole.

9. The system of claim 8, wherein the one or more electrophysiological sensors includes at least one from the group consisting of one or more electrogram and subcutaneous electrocardiogram sensors.

* * * * *